United States Patent
Jin et al.

(10) Patent No.: US 10,507,005 B2
(45) Date of Patent: Dec. 17, 2019

(54) SPECTRAL CALIBRATION OF SPECTRAL COMPUTED TOMOGRAPHY (CT)

(71) Applicant: GENERAL ELECTRIC COMPANY, Schenectady, NY (US)

(72) Inventors: Yannan Jin, Niskayuna, NY (US); Geng Fu, Rexford, NY (US); Peter M. Edic, Albany, NY (US); Hewei Gao, Pleasanton, CA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 186 days.

(21) Appl. No.: 15/273,043

(22) Filed: Sep. 22, 2016

(65) Prior Publication Data
US 2018/0078233 A1    Mar. 22, 2018

(51) Int. Cl.
*A61B 6/03*    (2006.01)
*A61B 6/00*    (2006.01)
(Continued)

(52) U.S. Cl.
CPC .............. *A61B 6/585* (2013.01); *A61B 6/032* (2013.01); *A61B 6/4241* (2013.01); *A61B 6/482* (2013.01);
(Continued)

(58) Field of Classification Search
CPC .. G01D 18/00; A61B 6/00; A61B 6/03; A61B 6/032; A61B 6/583; A61B 6/585; A61B 6/58; A61B 6/582
(Continued)

(56) References Cited

U.S. PATENT DOCUMENTS

| 6,848,827 B2 * | 2/2005 | Wu | ..................... A61B 6/583 378/19 |
| 7,086,780 B2 | 8/2006 | Wu et al. | |

(Continued)

FOREIGN PATENT DOCUMENTS

| WO | 2014/001984 A1 | 1/2014 |
| WO | 2014/121072 A2 | 8/2014 |

(Continued)

OTHER PUBLICATIONS

Alvarez, R.E., "Estimator for photon counting energy selective x-ray imaging with multibin pulse height analysis," Medical Physics, vol. 38, No. 5, pp. 2324-2334 (May 2011).
(Continued)

*Primary Examiner* — Jurie Yun (57) ABSTRACT

There is set forth herein a method including performing with an X-ray detector array of a CT imaging system one or more calibration scans, wherein the one or more calibration scans include obtaining for each element of the first through Nth elements of the X-ray detector array one or more calibration measurements; and updating a spectral response model for each element of the first through Nth elements using the one or more calibration measurements. In another aspect, a CT imaging system can perform imaging, e.g. including material decomposition (MD) imaging, using updated spectral response models for elements of an X-ray detector array. The spectral response models can be updated using a calibration process so that different elements of an X-ray detector array have different spectral response models.

20 Claims, 9 Drawing Sheets

(51) Int. Cl.
*G01T 7/00* (2006.01)
*G01N 23/046* (2018.01)
*G06T 11/00* (2006.01)
*G01T 1/169* (2006.01)

(52) U.S. Cl.
CPC .......... *A61B 6/583* (2013.01); *G01N 23/046* (2013.01); *G01T 1/169* (2013.01); *G01T 7/005* (2013.01); *G06T 11/003* (2013.01); *G01N 2223/3035* (2013.01); *G06T 2207/10081* (2013.01); *G06T 2211/40* (2013.01)

(58) Field of Classification Search
USPC ............................................. 378/18, 19, 207
See application file for complete search history.

(56) References Cited

U.S. PATENT DOCUMENTS

| | | | |
|---|---|---|---|
| 7,724,935 | B2 | 5/2010 | Van Stevendaal et al. |
| 7,869,566 | B2 | 1/2011 | Edic et al. |
| 8,315,352 | B2 | 11/2012 | Wu et al. |
| 8,611,627 | B2 | 12/2013 | Wu et al. |
| 9,020,092 | B2 | 4/2015 | Wang et al. |
| 9,155,516 | B2 | 10/2015 | Wang et al. |
| 9,274,066 | B2 | 3/2016 | Ji et al. |
| 2012/0087481 | A1 | 4/2012 | Litvin et al. |
| 2016/0033654 | A1 | 2/2016 | Tamura et al. |

FOREIGN PATENT DOCUMENTS

| | | |
|---|---|---|
| WO | 2014181315 A1 | 11/2014 |
| WO | 2016/076767 A1 | 5/2016 |

OTHER PUBLICATIONS

Liu, X., et al., "Spectral response model for a multibin photon-counting spectral computed tomography detector and its applications," Journal of Medical Imaging, vol. 2, No. 3, pp. 033502-1-033502-11 (Jul.-Sep. 2015).

Schlomka, J.P., et al., "Experimental feasibility of multi-energyphoton-counting K-edge imaging in pre-clinical computed tomography," Physics in Medicine and Biology, vol. 53, No. 15, pp. 4031-4047 (2008).

Schmidt, T.G., "An empirical method for correcting the detector spectral response in energy-resolved CT," Proc. of SPIE, vol. 8313, pp. 831312-1-831312-6 (2012).

International Search Report and Written Opinion issued in connection with corresponding PCT Application No. PCT/US2017/051096 dated Nov. 28, 2017.

Modgil et al., Basis Element Decomposition With Spectral MicroCT Using Multi-Layered, Multi-Colored Scintillation Detectors, Nuclear Science Symposium and Medical Imaging Conference (NSS/MIC), 2012 IEEE, Oct. 27-Nov. 3, 2012, pp. 3713-3716, Anaheim, CA.

Persson et al., A Framework for Evaluating Threshold Variation Compensation Methods in Photon Counting Spectral CT, IEEE Transactions on Medical Imaging, Oct. 10, 2012, pp. 1861-1874, vol. 31, Issue 10.

\* cited by examiner

SPECTRAL CALIBRATION OF SPECTRAL COMPUTED TOMOGRAPHY (CT)

The subject matter disclosed herein relates to non-invasive imaging and, in particular, to the use of Computed Tomography (CT) system imaging.

BACKGROUND

The subject matter disclosed herein relates to non-invasive imaging and, in particular, to spectral calibration of a radiographic imaging system.

In the fields of medical imaging and security screening, non-invasive imaging techniques have gained importance due to benefits that include convenience, and speed. In medical and research contexts, non-invasive imaging techniques are used to image organs or tissues beneath the surface of the skin. Similarly, in industrial or quality control (QC) contexts, non-invasive imaging techniques are used to examine parts or items for hidden defects that may not be evident from an external examination. In security screening, non-invasive imaging techniques are typically used to examine contents of containers (e.g., packages, bags, or luggage) without opening the containers and/or to screen individuals entering or leaving a secure location.

One example of a non-invasive imaging system is a computed tomography (CT) imaging system in which an X-ray source emits radiation (e.g., X-rays) towards an object or subject (e.g., a patient, a manufactured part, a package, or a piece of baggage) from a variety of different angular positions. The emitted X-rays, after being attenuated by the subject or object, typically impinge upon an array of radiation detector elements of an electronic detector, which generates signals indicative of the incident radiation at different locations on the detector. A gantry containing the X-ray source and radiation detectors may be rotated about the object, or the object may be rotated while the positions of X-ray source and radiation detectors are held fixed. The intensity of radiation reaching the detector is typically dependent on the X-ray spectrum emitted from the X-ray tube and the attenuation and absorption of X-rays through the scanned subject or object. The signals generated at the detector are processed to generate images and/or volumetric representations of the internal structures of the subject or object.

BRIEF DESCRIPTION

There is set forth herein a method including performing with an X-ray detector array of a CT imaging system one or more calibration scans, wherein the X-ray detector array includes individual detector elements and wherein the one or more calibration scans includes obtaining for each element of the first through Nth elements of the X-ray detector array one or more calibration measurements; and updating a spectral response model for each element of the first through Nth elements using for each respective element the one or more calibration measurements.

In another aspect, a CT imaging system can perform imaging, e.g. including material decomposition (MD) imaging, using updated spectral response models for elements of an X-ray detector array. The spectral response models can be updated using a calibration process so that different elements of an X-ray detector array have different spectral response models.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

There is set forth herein a method including performing with an X-ray detector array of a CT imaging system one or more calibration scans, wherein the one or more calibration scans includes obtaining for each element of the first through Nth elements one or more calibration measurements; and updating a spectral response model for each element of the first through Nth elements using for each respective element the one or more calibration measurements.

Figure 1:
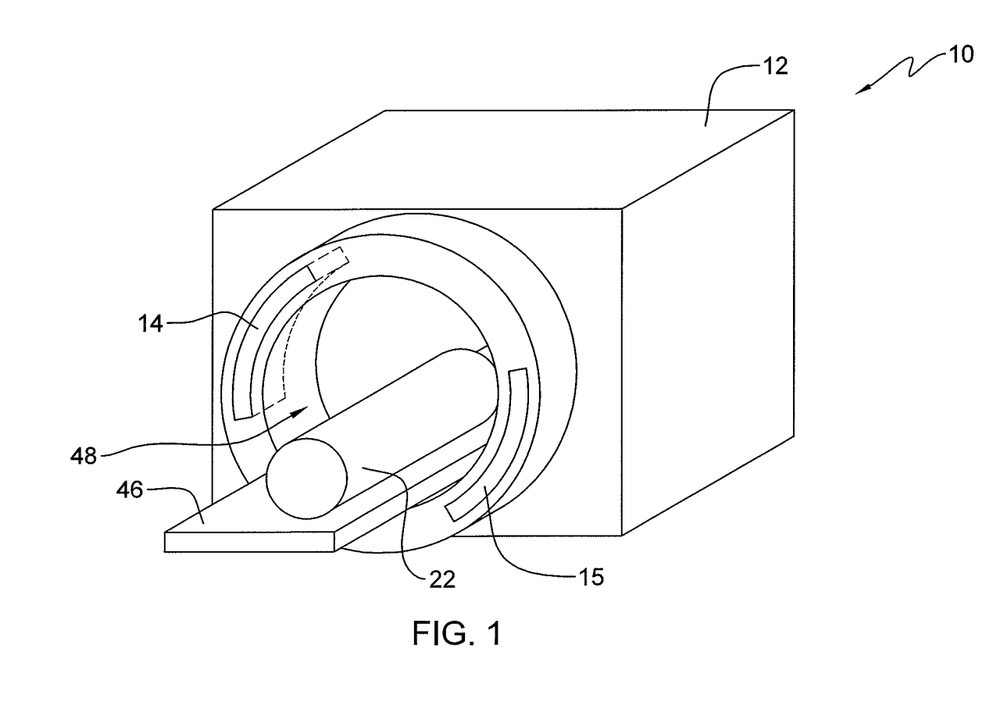
FIG. 1 is a physical perspective view of a CT imaging system.
Figure 2:
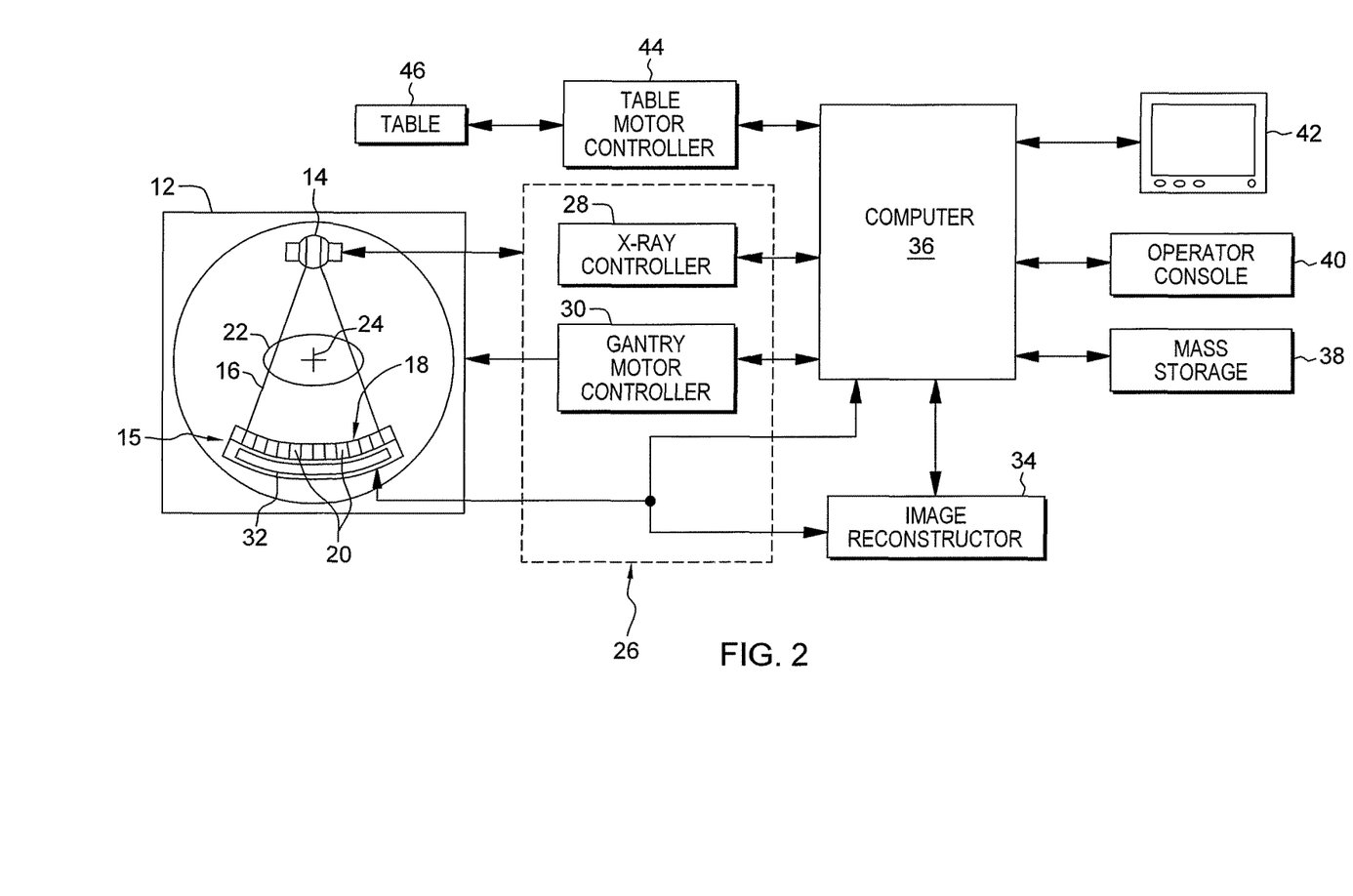
FIG. 2 is a block diagram of a CT imaging system illustrating an embodiment of the present disclosure.

Referring to FIG. 1 and FIG. 2, an exemplary computed tomography (CT) imaging system 10 is shown as including a gantry 12. Gantry 12 has an X-ray source 14 that projects a beam of X-rays 16 toward a detector assembly 15 on the opposite side of the gantry 12. The detector assembly 15 can include an X-ray detector array 18 having a plurality of elements 20, and data acquisition systems (DAS) 32. Detector assembly 15 can also include a collimator (not shown). The plurality of elements 20 detect the projected X-rays that pass through a medical patient disposed in an opening 48 of CT imaging system 10, and DAS 32 converts measurement data to digital signals for subsequent processing.

Each element 20 of CT imaging system 10 can produce an analog electrical signal that represents the intensity of an impinging X-ray beam and hence represents the attenuated beam as it passes through a patient, object, or, as depicted in FIG. 1, a spectral calibration phantom 22. During a scan to acquire X-ray projection data, gantry 12 and the components mounted thereon rotate about a center of rotation 24. Embodiments herein recognize that due to manufacturing tolerance, different elements 20 can respond differently when exposed to X-rays of varying energy levels. Non-uniformities in X-ray detector array 18 can result in imaging "artifacts" that misrepresent true characteristics of the object being imaged. In one embodiment, X-ray detector array 18 can be a cadmium zinc telluride (CZT) detector array. In one embodiment, X-ray detector array 18 can be a cadmium telluride (CdTe) detector array. Embodiments herein recognize that various types of X-ray detector array 18 including the noted types can include non-uniformities.

Rotation of gantry 12 and the operation of X-ray source 14 are governed by a control mechanism 26 of CT imaging system 10. Control mechanism 26 can include an X-ray controller 28 that provides power and timing signals to an X-ray source 14 and a gantry motor controller 30 that controls the rotational speed and position of gantry 12. An image reconstructor 34 can receive sampled and digitized X-ray data from DAS 32 and performs high-speed reconstruction. The high-speed reconstruction can include use of multi-energy projection data according to a material decomposition (MD) process as set forth herein.

The reconstructed images can be applied as an input to a computer 36, which can store the images in a mass storage device 38. Computer 36 can also store data from DAS 32 in mass storage device 38. Computer 36 also receives commands and scanning parameters from an operator via console 40. An associated display 42 allows the operator to observe the reconstructed images and other data from computer 36. The operator supplied commands and parameters are used by computer 36 to provide control signals and information to DAS 32, X-ray controller 28, and gantry motor controller 30. In addition, computer 36 can operate a table motor controller 44, which controls a motorized table 46 to position a patient or object undergoing imaging procedures (e.g., scanning of a patient or the spectral calibration phantom 22) within the gantry 12. Particularly, table 46 moves portions of the subject or other object through a gantry opening 48.

Figure 3:
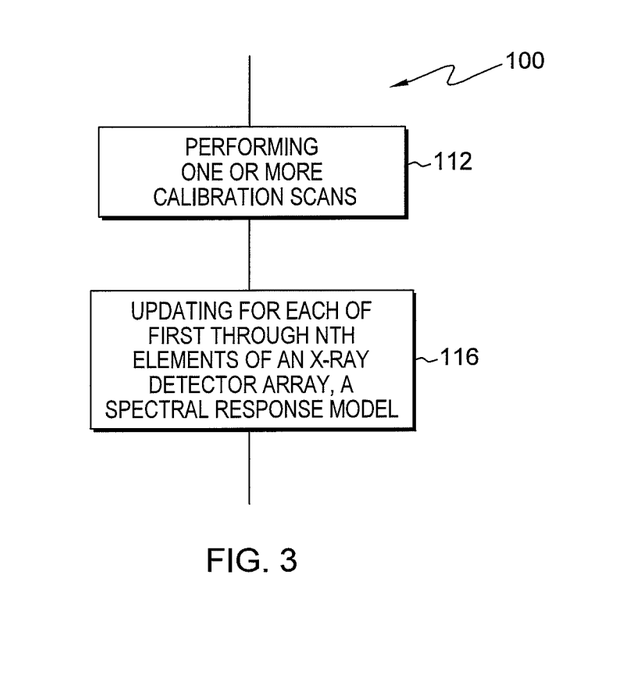
FIG. 3 is a flow diagram illustrating a method for calibrating the X-ray detector array in one embodiment of the detector array.

In reference to the flow diagram of FIG. 3 there is set forth herein a method 100 including performing at block 112 with an X-ray detector array 18 of a CT imaging system 10 one or more calibration scans to obtain one or more calibration measurements for each element of the first through Nth elements obtained at block 112, and updating at block 116 a spectral response model for the each of the first through Nth elements of an X-ray detector array 18 using the one or more calibration measurements for each respective element.

In one aspect, CT imaging system 10 can be configured to use one or more spectral response models to perform material decomposition (MD) for objects disposed in the CT imaging system 10, wherein the one or more spectral response models characterizes the spectral response for each respective element. In one embodiment, a calibration process can be performed to update spectral response models for the first through Nth elements of X-ray detector array 18. As a result of a calibration process set forth herein, different elements of X-ray detector array 18 can have different updated spectral response models that are provided through the calibration process. Methods herein can result in more accurate representations of a subject by way of processing techniques, which address non-uniformities of elements of an X-ray detector array 18.

In further reference to the method 100 described with reference to the flow diagram of FIG. 3, method 100 can include, prior to block 112, establishing an initial spectral response model for each of the first through Nth elements of an X-ray detector array 18.

Figure 4A:
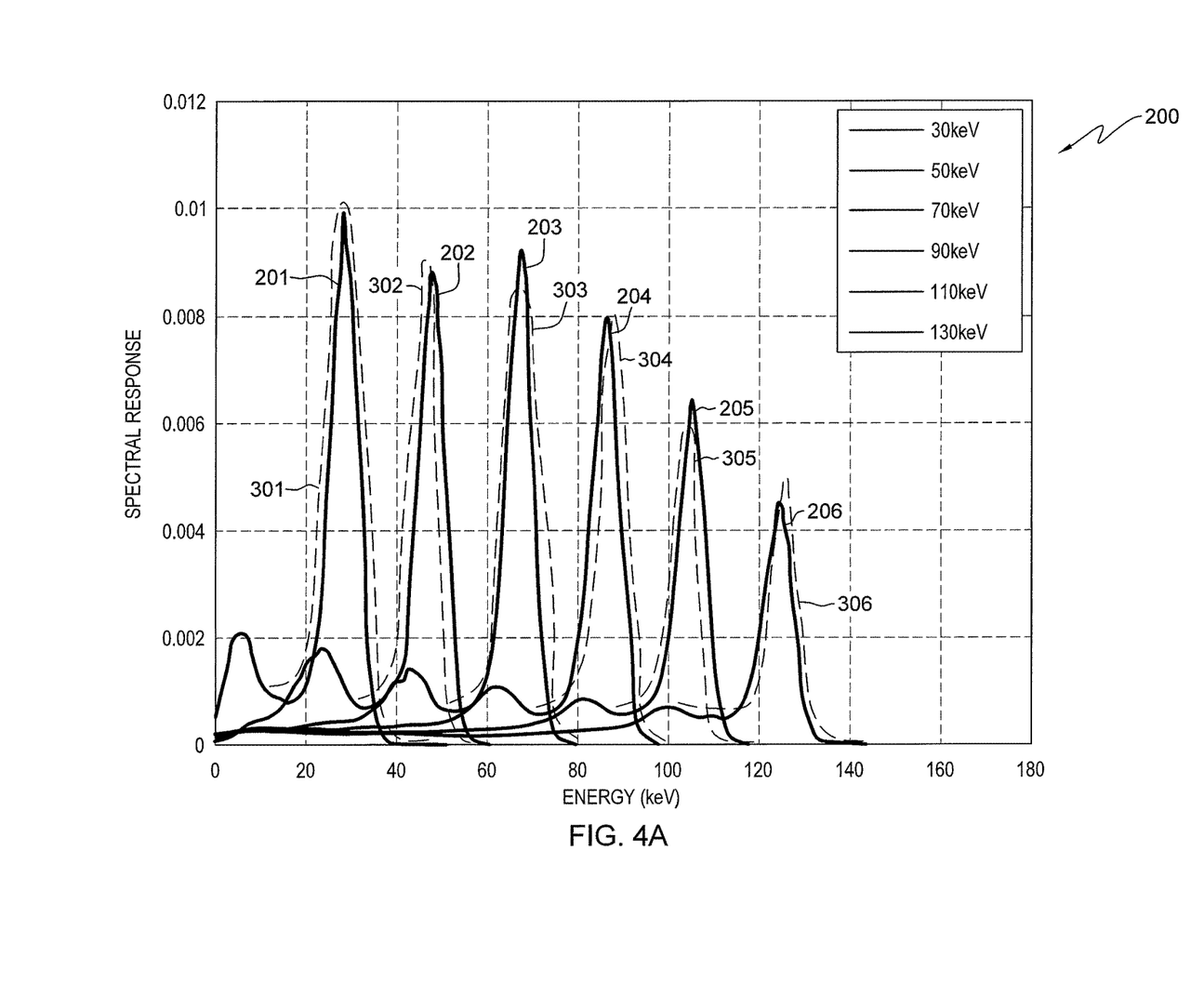
FIG. 4A is a plot of the spectral response model for an element.
Figure 4B:
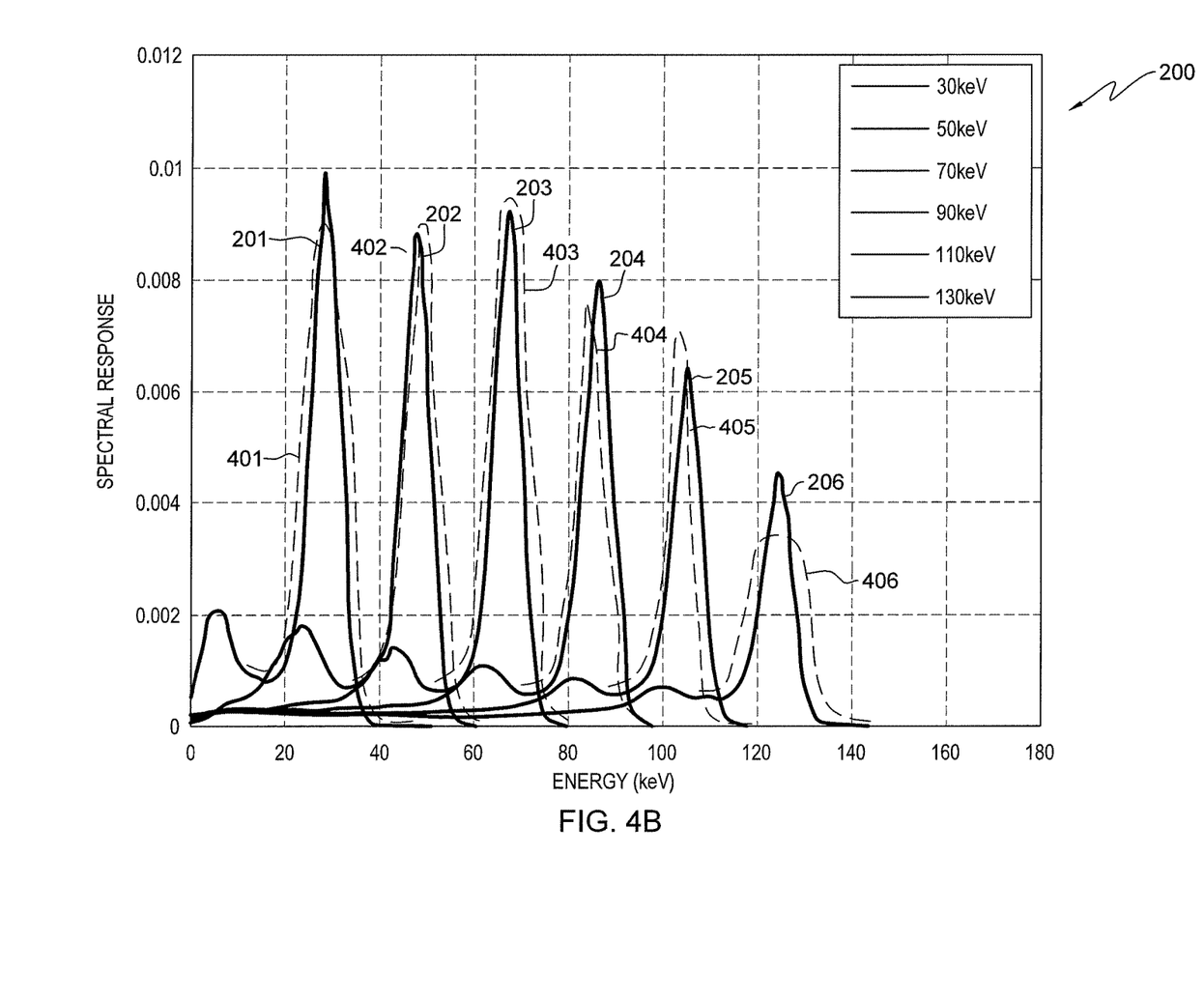
FIG. 4B is a plot of the spectral response model for an element.

An illustrative spectral response model 200 for an element is set forth in FIGS. 4A and 4B. A spectral response model 200 can include for each of several hypothetical narrow-band illumination energy levels (a narrow-band energy level ideally corresponds to a single energy level) an element's expected spectral response, for example, spectral response profile 201 for a illumination energy level, a second spectral response profile 202 for a second illumination energy level, a third spectral response profile 203 for a third illumination energy level, a fourth spectral response profile 204 for a fourth illumination energy level, a fifth spectral response profile 205 for a fifth illumination energy level, a sixth spectral response profile 206 for a sixth illumination energy level, and so forth. Establishing a spectral response model can include establishing a spectral response model based on detector design features such as detector size, detector pitch, the detector's sensor material thickness, shaping time of associated electronics, and the applied voltage across the sensor.

In one embodiment, a Monte Carlo simulation can be performed for establishing an initial spectral response model. Inputs to a Monte Carlo simulation can include the energy of the incident X-ray photon, the sensor material (including X-ray absorption efficiency and charge transport lifetime and mobility), the sensor thickness, the size of the electron cloud generated by the interacting X-ray photon, the applied voltage across the sensor, the size of the detector element, the distance between neighboring elements, and the noise level in the detector. Establishing an initial spectral response model can include use of processes in addition to or in the alternative to use of a Monte Carlo simulation, e.g., can include one or more of use of an analytical model or use of measurements with a synchrotron source. In the representation of FIGS. 4A and 4B, a spectral response model is represented as including six discrete spectral response profiles for different energy levels. However, skilled artisans will recognize that a spectral response model can be established using functions representing spectral response profiles for a continuum of energy levels. A resolution or sampling for a spectral response model can be selected based on, for example, available processing resources and/or processing time requirements.

Establishing a spectral response model can include establishing tuning parameters for a spectral response model. In one aspect a spectral response model can be expressed in terms of tuning parameters. For example, each spectral response profile 201-206 can be regarded to include a Gaussian profile component (right hand side) and tail profile component (left hand side). The tail component can be attributable to charge sharing from a neighboring element and escape of fluorescent X-rays from the sensor material to neighboring elements. The Gaussian profile section can be expressed in terms of one or more tuning parameters, e.g. mean (location of peak) and standard deviation (related to width). The tail section of the spectral response profile can be expressed in the terms of one or more tuning parameters, e.g. a linear tangent value. The tuning parameters of a spectral response model can be tuned with performance of a calibration process as set forth herein.

Figure 5:
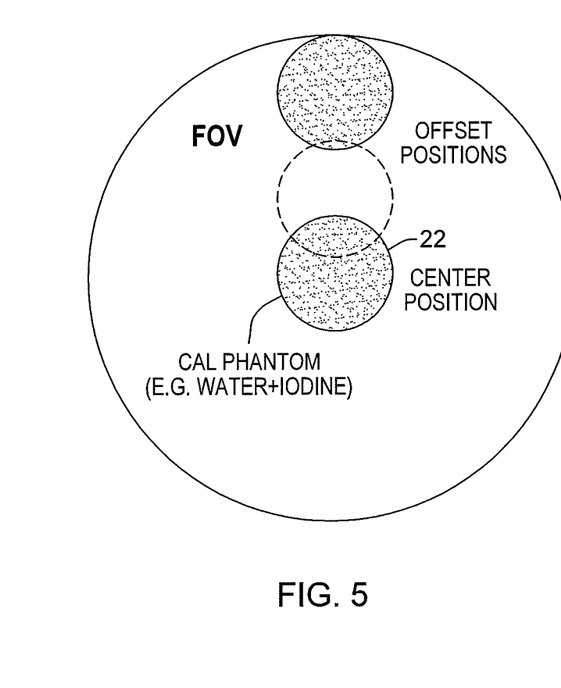
FIG. 5 is a schematic diagram illustrating employment of a calibration phantom in a CT imaging system.

In further reference to method 100 further details relative to block 112 (performing one or more calibration scans) are now described. Performance of one or more scans at block 112 can include performance of one or more scans with calibration phantom 22 being disposed in the CT imaging system 10 as illustrated schematically in FIG. 5. In one embodiment performing one or more calibration scans can include using a calibration phantom 22 at the center position within the scan field of view (FOV) and multiple offset positions. In one embodiment performing one or more calibration scans can include using more than one calibration phantoms 22.

Performance of one or more calibration scans at block 112 can include performance of a single scan using a single calibration phantom 22. During a calibration scan a calibration output measurement signal can be obtained for the first though Nth elements of an X-ray detector array 18. Calibration phantom 22 can include, for example, water and/or iodine.

Figure 6:
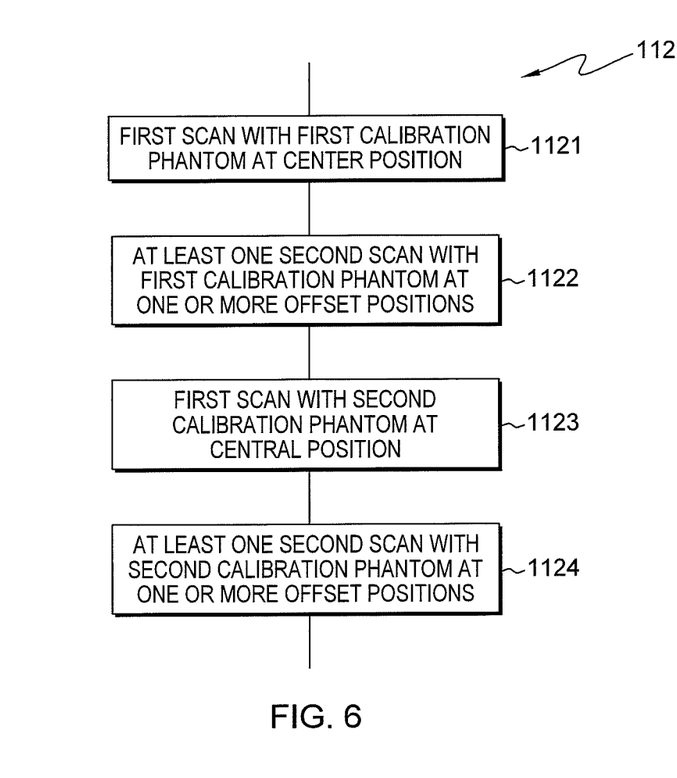
FIG. 6 is a flow diagram illustrating performance of a calibration signal collection routine in one embodiment.

Performance of one or more calibration scans (block 112) in another embodiment is described in further detail in reference to the flow diagram of FIG. 6. At block 1121 a first calibration scan can be performed with a first calibration phantom (e.g. including water) disposed at a center position. At block 1122 at least one second calibration scan can be performed with the first calibration phantom (e.g. including water) disposed at one or more offset positions. At block 1123 a first calibration scan can be performed with a second calibration phantom (e.g. including iodine) disposed at a center position. At block 1124 at least one second calibration scan can be performed with a second calibration phantom (e.g. including iodine) disposed at one or more offset positions. During each of the calibration scans referenced in the flow diagram of FIG. 6 one or more calibration measurements for each element of the first through Nth elements can be obtained from X-ray detector array 18 by readout of X-ray detector array 18. For each calibration scan, a scan angle can be changed multiple times by rotation of the gantry 12. In instances herein where a calibration phantom including iodine is described, iodine can be replaced with another substance having a high atomic number, e.g. atomic number 20 or greater. In general, one or more phantoms containing one or more materials may be positioned at one or more positions with the scan field of view to acquire the required calibration measurements to utilize the processing methods disclosed herein.

In further reference to method 100, method 100 at block 116 can update a spectral response model for each element of X-ray detector array 18. Referring again to FIG. 4A there is schematically illustrated an updated spectral response model. Referring to FIG. 4A, an initial spectral response model can include a set of spectral response profiles 201-206. For each energy level of the spectral response model 200 as shown in FIG. 4A, the spectral response model can be updated as indicted by spectral response profiles 301-306 illustrating in one embodiment an exemplary updating of spectral response profiles at different illumination energy levels. FIG. 4B illustrates a spectral response model for another element that can be updated at block 116. Referring to FIG. 4B another element of X-ray detector array 18 can have a spectral model updated differently than the spectral model for another element, as indicated by the updated spectral response profiles 401-406.

Aspects of updating at block 116 in one embodiment are further set forth as follows. Embodiments herein recognize that if a spectral response model for an element is established perfectly, then the output of an X-ray detector array 18 under a specific scanning condition would be precisely known (the predicted value of the calibration measurement). However, due to manufacturing and system set-up tolerances, the actual calibration measurement of an element can deviate from a predicted value. Embodiments herein operate to update spectral response models for the first through Nth elements of X-ray detector array 18 so that the spectral response model more accurately represents the functioning of each element and characterizes non-uniformities in functional aspects between elements. Updating a spectral response model at block 116 can include for each of the first through Nth elements of an X-ray detector array 18 repeatedly updating an output calibration spectral response model from data acquired from a sequence of scan angles for one or more scans. A most recently updated calibration spectral response model can be used for performance of imaging subsequent to block 116.

In one embodiment, CT imaging system 10 can use a forward-model process for determining an updated spectral response model for an element of X-ray detector array 18. A forward-model process can use both predicted values for calibration measurements and actual calibration measurements. Aspects of a forward-model procedure for updating a spectral response model are set forth in reference to the flow diagram of FIG. 7.

Figure 7:
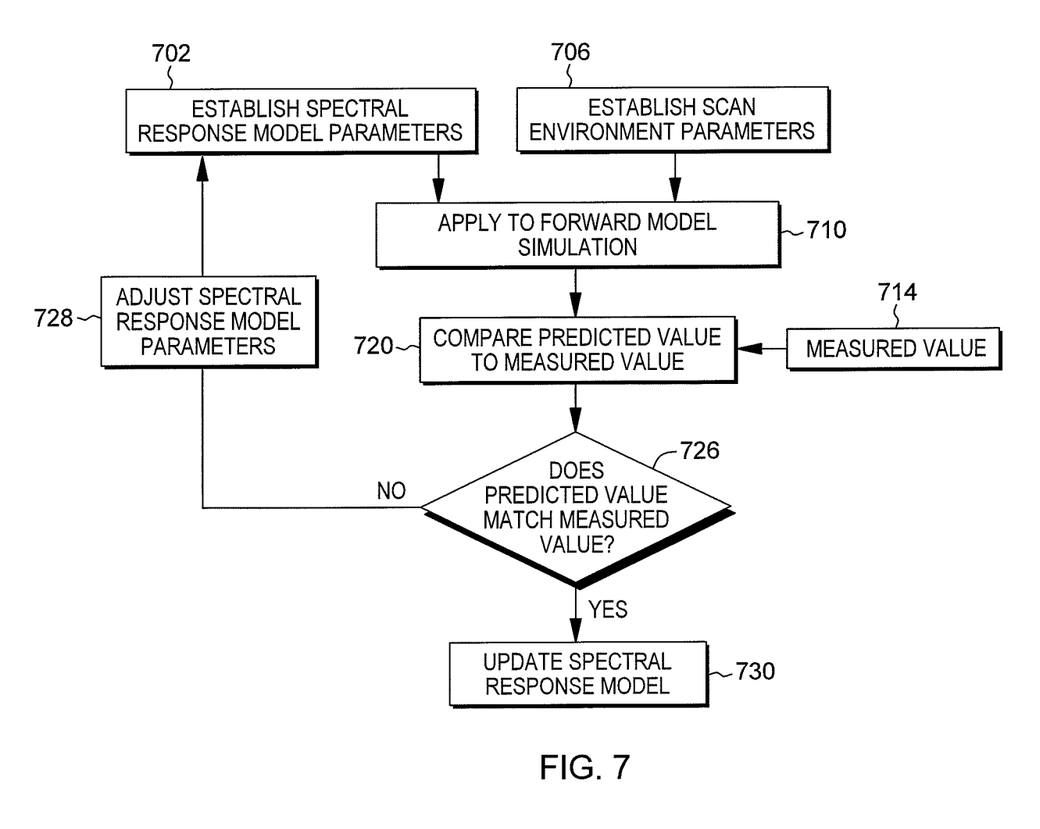
FIG. 7 is a flow diagram illustrating updating of a spectral response model in one embodiment.

Referring to blocks 702 and 706 and 710, system 10 can determine predicted values for calibration measurements for a certain element under current scanning conditions by establishing tuning parameters of the spectral response model and utilizing scan environment parameters in a forward model of the system. Referring to block 714 system 10 can obtain calibration measurements for a certain element e.g., in accordance with block 112.

At block 720, system 10 can compare predicted and actual calibration measurements and at decision block 726 system 10 can determine if a predicted value for calibration measurements for a current element matches actual calibration measurements as output at block 714. For system 10, determining that there is a match at block 726 system 10 can apply at least one matching criteria. According to the matching criteria in one embodiment a predicted value for a calibration measurement need not be identical to an actual calibration measurement but can resemble, e.g., be statistically similar to an actual calibration measurement. If system 10 at block 726 determines that there is a match between a predicted value for calibration measurements and actual calibration measurements, system 10 at block 730 can select the spectral response model yielding the match as the updated calibration spectral response model for the current element. Otherwise, the tuning parameters in the spectral response model can be adjusted at block 728 and, at block 702, the established parameters can be based on the adjusted parameters adjusted at block 728, and the process flow repeated until the matching criteria is satisfied.

Aspects of blocks 702, 706 and 710 for output of predicted element signal values are now further described. At block 702, system 10 can establish forward-model tuning parameters for a spectral response model of a certain element, e.g., a certain element of the first through Nth elements of X-ray detector array 18. The forward-model tuning parameters can be selected according to the spectral response model tuning parameters described with reference to FIGS. 4A and 4B, e.g. one or more tuning parameters for modeling a Gaussian section of a spectral response profile and one or more tuning parameters for modeling a tail section of a spectral response profile. At block 706, system 10 can establish variable parameters for modeling a current scanning environment such as parameters for modeling a calibration phantom 22 and operating parameters (operating tube voltage and operating tube current) of X-ray source 14. Parameters can model both a material of phantom 22 and an offset within the scan field of view for calibration phantom 22. At block 710, system 10 can perform a simulation (forward model) to determine predicted output values for calibration measurements. A simulation can include performing a convolution of a spectral response model (block 702) and an environment model (block 706). At block 720, system 10 can compare predicted values for calibration measurements and actual calibration measurements. A spectral response model established by system 10 at block 702 can be an initial spectral response model in the case the forward-model procedure of the flow diagram of FIG. 7 is being performed a first time for a certain element during an initial calibration of system 10. Otherwise, the spectral response model can be a spectral response model having tuned spectral response model tuning parameters, e.g. updated or adjusted tuning parameters as set forth herein.

If system 10 at block 726 determines that there is a match between predicted values for calibration measurements and actual calibration measurements, system 10, at block 730, can select the spectral response model yielding the match as an updated spectral response model for the certain element. For selection of the spectral response model, the spectral response model tuning parameters yielding the match determined at block 726 and defining the matching spectral response model can be flagged. When a spectral response model is selected at block 730, system 10 can proceed and perform again the procedure of the flow diagram of FIG. 7 for another element, e.g., for a sequence of scan angles of a current scan, for a sequence of scan angles of a next scan as may be required by a calibration. A spectral response model for a certain element can be repeatedly updated for a sequence of scan angles of each scan as required for a calibration e.g. for all calibration phantoms of one or more calibration phantoms 22 and for the center and one or more offset positions for the one or more calibration phantoms. The forward-model procedure illustrated with reference to the flow diagram of FIG. 7 can be repeated for each of the first through Nth elements of an X-ray detector array 18.

If system 10 at block 726 determines that there is not a match between predicted values for calibration measurements and actual calibration measurements, system 10 can at block 728 adjust spectral response model tuning parameters of the spectral response model to new values and spectral response model tuning parameters at block 702 can be established based on the adjusted values. System 10 can employ analytics (e.g. least-square fitting) and/or iterative (e.g. maximum likelihood) methods to adjust at block 728 the spectral response model tuning parameters until the simulated data using the forward model resembles the measured data.

One or more calibration scans as referred at block 112 can include more than one calibration scans and each calibration scan can include scanning at multiple scan angles. In the performance of a calibration process having a single calibration scan, a calibration spectral response model for a certain element can be updated for a sequence of scan angles of the single scan. In the performance of a calibration process having multiple calibration scans (e.g. using multiple calibration phantoms 22 and/or multiple positions of a calibration phantom 22) the spectral response model for a certain element can be updated for a sequence of scan angles for each scan of a collection of scans—either separately or collectively. The method described in connection with FIG. 7 can be carried out for each of the first through Nth elements of an X-ray detector array 18. The first though Nth elements can refer to all elements of X-ray detector array 18, a subset of elements of the X-ray detector array 18 that comprise an adjacent set of elements, a non-adjacent set of elements, a set of elements having adjacent and non-adjacent elements, or a random sampling of elements of X-ray detector array 18.

For updating a spectral response model for a set of the first through Nth elements at block 116 in one embodiment (FIG. 3), system 10 can repeatedly update a spectral response model for each respective element of X-ray detector array 18. As set forth herein, system 10 can use calibration measurement signals of respective elements for updating a spectral response model for the respective elements.

In further reference to method 100 as set forth in the flow diagram of FIG. 3, method 100 subsequent to block 116 can include performing imaging of an object such a human subject. Performing imaging can include performing material decomposition (MD) using the spectral response model for each respective element of the first through Nth elements as updated at block 116. MD can be performed by system 10 for improving CT imaging performance. System 10 can be activated to perform a CT scan and responsively imaging system 10 can output a CT scan image using determined MD information. In one embodiment, system 10 can output MD information in the form of basis material projections, e.g. water and iodine projections, which can be used by image reconstructor 34 to perform image reconstruction. In one embodiment performance of imaging can include performance of MD and/or performance of image reconstruction.

One example of a function that can be used to perform material decomposition (MD) is the following.

$$\vec{A} = \arg\min_{\vec{A}} \sum_{i=1}^{N} \left[ \lambda_i(\vec{A}) - N_i \ln \lambda_i(\vec{A}) \right] \quad \text{Eq. 1}$$

where $\vec{A}$ is a vector of area density estimates for the collection of basis materials, $\lambda_i$ is the photon counts in the $i^{th}$ energy bin.

The calculation of $\lambda_i$ from $\vec{A}$ (an M-dimensional vector of the area density estimates for each of M basis materials) is based on the forward model of the CT imaging system:

$$\lambda_i(\vec{A}) = \int S_i(E)\Phi(E)D(E)e^{-\int \mu(\vec{x},E)ds}dE \quad \text{Eq. 2}$$

where $S_i(E)$ refers to the spectral response, $\Phi(E)$ refers to the source spectrum, and $D(E)$ refers to the detection efficiency of the detector element.

$$S_i(E) = \int_{T_{i-1}}^{T_i} R(E,E')dE' \quad \text{Eq. 3}$$

where $R(E,E')$ is the element-by-element calibrated spectral response function; $T_{i-1}$ and $T_i$ are the energy thresholds of the $i^{th}$ energy bin.

The attenuation coefficient $\mu(\vec{x},E)$ is defined as $$\mu(\vec{x},E) = \sum_{a=1}^{M} a_a(\vec{x}) \cdot f_a(E) \quad \text{Eq. 4}$$

where $a_a(\vec{x})$ is the density distribution and $f_a(E)$ is the mass attenuation coefficient, M is the total number of basis materials. Thus the line integral in Eq. 2 can be written as $$\int \mu(\vec{x},E)ds = \sum_{a=1}^{M} A_a \cdot f_a(E) \quad \text{Eq. 5}$$

where $$A_a = \int a_a(\vec{x})ds \quad \text{Eq. 6}$$

refers to the material density integral which is the definition of material area density.

Figure 8:
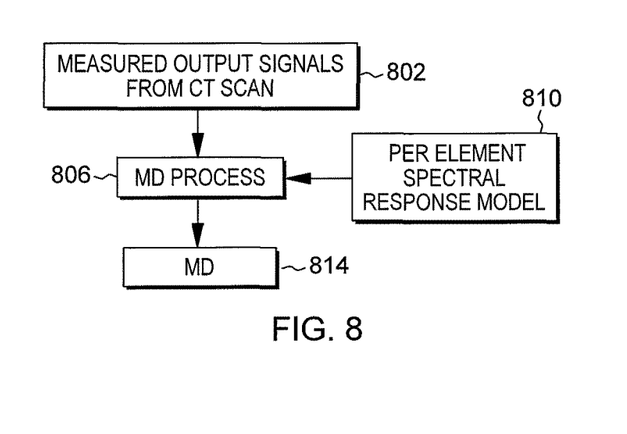
FIG. 8 is a flow diagram illustrating obtaining of material decomposition (MD) parameters.

A method for performing material decomposition encompassing the processes of the flow diagram of FIG. 7 and Equations 1-6 is set forth in reference to the flow diagram of FIG. 8. At block 802 referring to the flow diagram of FIG. 8, system 10 can output measurement signals for each detector element from a CT scan. A human body can be disposed in CT imaging system 10 for example during the performance of a CT scan. At block 806, system 10 can perform MD processing using the measurement signals for each detector element output at block 802 and a spectral response model at block 810 for output of MD information at block 814, e.g. area density estimates of basis materials distributions. Referring to block 810 a spectral response model can be input into MD processing block 806. The spectral response model referred to at block 810 can be per element spectral response models, meaning that the spectral response model can be differentiated between elements. Per element spectral response models can be updated as described in connection with the flow diagram of FIG. 7. Accordingly, spectral response models that are updated according to the calibration process referred to at block 112 and block 116 can be differentiated between elements. In one embodiment, an updated spectral response model for a certain element used in an MD process can be a most recently updated spectral response model for the certain element, e.g., the updated spectral response model as updated at a conclusion of a calibration process described in one embodiment in reference to the flow diagrams of FIGS. 3, 6, and 7.

Referring to FIG. 4A, an initial spectral response model can include a set of spectral response profiles 201-206 and an arbitrary element of the first through Nth elements of X-ray detector array 18 can be updated from the initial spectral response model having spectral response profiles 201-206 as an updated set of spectral response profiles 301-306 as shown in FIG. 4A. Referring to FIG. 4B, an initial spectral response model can include a set of spectral response profiles 201-206 and a second arbitrary element of the first through Nth elements of X-ray detector array 18 can be updated, e.g. using a calibration process described with reference to the flow diagrams of FIGS. 3, 6 and 7, from the initial spectral response model having profiles 201-206 as an updated set of spectral response profiles 401-406 as shown in FIG. 4B. Comparing FIGS. 4A and 4B, updated spectral response models 200 can be differentiated between elements to permit accurate imaging that can compensate for the fact that different elements may have different and non-uniform characteristics due to manufacturing tolerances and material properties; these characteristics cause the elements to respond to radiant energy differently.

Figure 9:
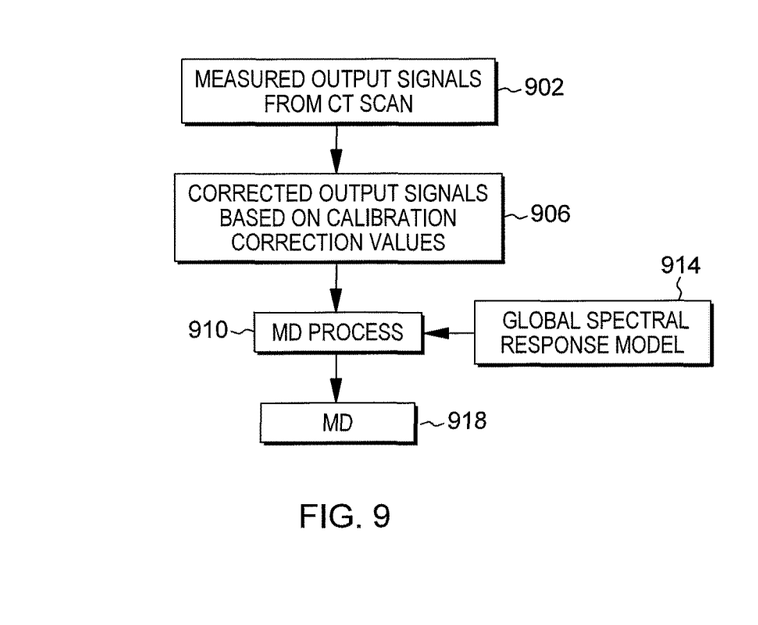
FIG. 9 is a flow diagram illustrating obtaining of MD parameters.

An alternative method for performing material decomposition (MD) is set forth in reference to the flow diagram of FIG. 9. At block 902, system 10 can output measurement signals for each detector element from a CT scan. A subject, e.g. a human body, can be disposed in a CT imaging system 10 during the performance of a CT scan. At block 906, system 10 can correct measurement values for each detector element using correction values as determined during a prior calibration process. At block 910, the corrected measurement values for each detector element can be used as input into an MD process indicated by block 910. Also input into the MD process indicated by block 910 can be a spectral response model as indicated by block 914. MD information, e.g. in the form of basis material density projections, can be output at block 918, e.g. area density estimates of basis material distributions. The spectral response model indicated at block 914 can be a global element spectral response model that is not differentiated between elements of X-ray detector array 18.

Embodiments herein recognize that significant benefits can be derived by providing an spectral response model for detector elements that is differentiated between elements so that differences in physical characteristics between elements are accounted for and can be corrected for. The modeling of different elements differently can provide for more accurate, higher signal-to-noise ratio, and/or higher-resolution imaging. Although discussed in the context of CT imaging, the embodiments herein may be applied to any X-ray detector, e.g. an X-ray detector used for radiographic imaging.

Technical effects of the invention can include spectral calibration of a CT system using a calibration phantom that is scanned. Other technical effects include updating a spectral response model using calibration measurements. Other technical effects can include use of a certain calibration phantom in a calibration process. Other technical effects can include use of a method for providing spectral response models for detector elements wherein first and second different elements are modeled differently in order to compensate for element non-uniformities.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method comprising:
    (a) performing one or more calibration scans with an X-ray detector array of a CT imaging system, wherein the one or more calibration scans includes obtaining for each element of a first through Nth elements of the X-ray detector array one or more calibration measurements; and
    (b) updating for the each of the first through Nth elements of the X-ray detector array of the CT imaging system a spectral response model for the purpose of material decomposition, using the one or more calibration measurements for each respective element of the first through Nth elements, the updating resulting in an updated spectral response model for each element of the first through Nth elements, wherein the CT imaging system is configured to use the updated spectral response model for each element of the first through Nth elements for performance of imaging.

2. The method of claim 1, wherein establishing of an initial model for the spectral response model includes use of one or more of the following selected from the group consisting of: a Monte Carlo simulation, an analytics model, and a measurement with a synchrotron source.

3. The method of claim 1, wherein the spectral response model for a certain element of the first through Nth elements characterizes a spectral response of the certain element under illumination by a narrow-band source.

4. The method of claim 1, wherein the spectral response model for each of the first through Nth elements is established in dependence on one or more physical characteristics of the detector element.

5. The method of claim 1, wherein the performing one or more calibration scans includes performing a calibration scan using one or more calibration phantoms in one or more positions within a scan field of view, the calibration phantom including a material having an atomic number greater than or equal to 20.

6. The method of claim 1, wherein the performing one or more calibration scans includes performing a calibration scan using a first scan of one or more calibration phantoms in one or more positions within a scan field of view, the first scan of one or more calibration phantoms including a first set of materials and performing a second scan using one or more calibration phantoms in one or more positions within the scan field of view, the second scan of one or more calibration phantoms including a second set of materials.

7. The method of claim 1, wherein the performing one or more calibration scans includes performing at least one scan with a calibration phantom disposed at a first position, and performing additional scans with the calibration phantom offset from the first position.

8. The method of claim 1, wherein the method includes performing the one or more calibration scans and the updating repeatedly to compensate for spectral non-uniformities.

9. The method of claim 1, wherein the updating includes employing a forward-model process wherein predicted values for calibration measurements are compared to actual calibration measurements.

10. The method of claim 1, wherein the updating includes employing a forward-model process wherein predicted values for calibration measurements for a certain element are compared to actual calibration measurements, wherein a spectral response model yielding a resemblance is selected as an output spectral response model for the certain element.

11. The method of claim 1, wherein the updating includes employing a forward-model process wherein predicted values for calibration measurements for a certain element are compared to actual calibration measurements, wherein a spectral response model yielding a resemblance is selected as an updated spectral response model for the certain element, and wherein a most recent updated spectral response model for the certain element is used in the performance of imaging.

12. The method of claim 1, wherein the method includes establishing one or more tuning parameters for a spectral response model for a certain element of the first through Nth elements.

13. The method of claim 12, wherein the one or more tuning parameters include one or more tuning parameters for modeling a Gaussian section of a spectral response profile, and one or more tuning parameters for modeling a tail portion of the spectral response profile.

14. The method of claim 1, wherein the updating a spectral response model for each respective element of the first through Nth elements includes repeatedly updating the spectral response model, for each element of the first through Nth elements.

15. The method of claim 14, wherein the updated spectral response model for each element of the first through Nth elements is a most recently updated spectral response model that is most recently updated at a conclusion of a calibration process.

16. The method of claim 1, wherein the material decomposition comprises use of multi-energy projection data.

17. A CT imaging system comprising:
an X-ray detector array;
a data acquisition system (DAS) coupled to the X-ray detector array; and
a computer coupled to the DAS;
wherein the CT imaging system is operative for obtaining one or more calibration measurements from the X-ray detector array and the DAS to generate an updated spectral response model by the computer for the purpose of material decomposition for each of a first through Nth elements of the X-ray detector array;
wherein the CT imaging system is operative to use the updated spectral response model generated by the computer for each of the respective first though Nth elements for performance of imaging, and wherein the spectral response model is differentiated between elements of the first through Nth elements.

18. The system of claim 17, wherein the material decomposition comprises use of multi-energy projection data.

19. A method comprising:
(a) performing one or more calibration scans with an X-ray detector array of a CT imaging system, wherein the one or more calibration scans include disposing one or more calibration phantoms in one or more positions within a scan field of view within the CT imaging system and obtaining for each element of a first through Nth elements one or more calibration measurements, wherein the calibration phantom includes material having an atomic number of at least 20; and
(b) utilizing calibration information using the one or more calibration measurements for each element to generate an updated spectral response model for the purpose of material decomposition for each element, wherein the CT imaging system is configured to use the updated spectral response model for each element of the first through Nth elements for performance of imaging.

20. The method of claim 19, wherein the material decomposition comprises use of multi-energy projection data.

* * * * *